(12) United States Patent
Yeo et al.

(10) Patent No.: US 11,138,707 B2
(45) Date of Patent: Oct. 5, 2021

(54) ELECTRONIC DEVICE AND METHOD FOR PROCESSING MULTIPLE IMAGES

(71) Applicant: Samsung Electronics Co., Ltd., Gyeonggi-do (KR)

(72) Inventors: Dongwon Yeo, Seoul (KR); Minkyu Park, Seoul (KR); Kihuk Lee, Gyeonggi-do (KR)

(73) Assignee: Samsung Electronics Co., Ltd

( * ) Notice: Subject to any disclaimer, the term of this patent is extended or adjusted under 35 U.S.C. 154(b) by 126 days.

(21) Appl. No.: 16/330,976

(22) PCT Filed: Sep. 5, 2017

(86) PCT No.: PCT/KR2017/009720
§ 371 (c)(1),
(2) Date: Mar. 6, 2019

(87) PCT Pub. No.: WO2018/048177
PCT Pub. Date: Mar. 15, 2018

(65) Prior Publication Data
US 2019/0236765 A1      Aug. 1, 2019

(30) Foreign Application Priority Data
Sep. 6, 2016   (KR) .................. 10-2016-0114462

(51) Int. Cl.
G06T 5/50 (2006.01)
G06T 5/00 (2006.01)
H04N 5/232 (2006.01)

(52) U.S. Cl.
CPC .............. *G06T 5/50* (2013.01); *G06T 5/002* (2013.01); *G06T 5/003* (2013.01); *G06T 5/009* (2013.01);
(Continued)

(58) Field of Classification Search
None
See application file for complete search history.

(56) References Cited

U.S. PATENT DOCUMENTS

2010/0171837 A1   7/2010   Pillman et al.
2011/0169921 A1   7/2011   Lee et al.
(Continued)

FOREIGN PATENT DOCUMENTS

| KR | 1020110082736 | 7/2011 |
| KR | 1020140060760 | 5/2014 |
| KR | 1020160012743 | 2/2016 |

OTHER PUBLICATIONS

PCT/ISA/210 Search Report issued on PCT/KR2017/009720 (pp. 5).
PCT/ISA/237 Written Opinion issued on PCT/KR2017/009720 (pp. 6).

*Primary Examiner* — Samah A Beg
(74) *Attorney, Agent, or Firm* — The Farrell Law Firm, P.C.

(57) ABSTRACT

A method for processing multiple images according to various embodiments of the present invention may comprise the operations of: acquiring multiple images by using multiple cameras; extracting image information for each of the acquired multiple images; preprocessing the multiple images on the basis of the extracted image information, and generating parameters corresponding to the multiple images, respectively; selecting one or more images required according to a zoom magnification among the acquired multiple images; and applying parameters corresponding to the selected one or more images and performing image processing. Other embodiments are possible.

8 Claims, 7 Drawing Sheets

(52) U.S. Cl.
CPC ... *H04N 5/23212* (2013.01); *H04N 5/232122* (2018.08); *G06T 2207/20221* (2013.01)

(56) References Cited

U.S. PATENT DOCUMENTS

| | | | | |
|---|---|---|---|---|
| 2011/0234977 | A1* | 9/2011 | Verdooner | A61B 3/145 351/207 |
| 2012/0274815 | A1* | 11/2012 | Matsumoto | H04N 5/23216 348/240.99 |
| 2013/0258130 | A1* | 10/2013 | Mihara | G02B 15/1461 348/222.1 |
| 2013/0329088 | A1* | 12/2013 | Blayvas | H04N 5/23212 348/239 |
| 2014/0002606 | A1* | 1/2014 | Blayvas | G02B 27/0075 348/46 |
| 2014/0043435 | A1* | 2/2014 | Blayvas | H04N 13/236 348/46 |
| 2014/0085515 | A1* | 3/2014 | Blayvas | H04N 9/04517 348/242 |
| 2015/0029357 | A1 | 1/2015 | Hamalainen | |
| 2015/0055886 | A1* | 2/2015 | Oh | H04N 5/23238 382/284 |
| 2015/0085174 | A1* | 3/2015 | Shabtay | H04N 9/097 348/336 |
| 2015/0097981 | A1 | 4/2015 | Griffith et al. | |
| 2015/0109484 | A1* | 4/2015 | Laroia | G02B 7/282 348/240.3 |
| 2015/0304557 | A1 | 10/2015 | Choi | |
| 2016/0028949 | A1* | 1/2016 | Lee | H04N 5/23296 348/218.1 |
| 2016/0050374 | A1* | 2/2016 | Shabtay | H04N 5/23296 348/240.3 |
| 2016/0119550 | A1* | 4/2016 | Tsutsumi | H04N 5/23229 348/239 |
| 2018/0070018 | A1* | 3/2018 | Bian | H04N 5/247 |

\* cited by examiner

ELECTRONIC DEVICE AND METHOD FOR PROCESSING MULTIPLE IMAGES

PRIORITY

This application is a National Phase Entry of PCT International Application No. PCT/KR2017/009720 which was filed on Sep. 5, 2017, and claims priority to Korean Patent Application No. 10-2016-0114462, which was filed on Sep. 6, 2016, the content of each of which is incorporated herein by reference.

TECHNICAL FIELD

Embodiments of the disclosure relate to a method for displaying images acquired by a plurality of cameras and an electronic device implementing the same.

BACKGROUND ART

The remarkable development of information and communication technologies and semiconductor technologies has brought about a sharp increase in the spread and use of electronic devices. These electronic devices have converged to provide various functions, as well as providing traditional and unique functions thereof. For example, electronic devices provide a camera function of photographing objects and generating and storing images or videos. For example, the electronic devices are equipped with one or more cameras in various types.

DISCLOSURE OF INVENTION

Technical Problem

The electronic device may acquire various types of images using a plurality of cameras. Processing of images acquired by a plurality of cameras requires more power consumption and memory consumption than a single image is processed.

As a method of utilizing a plurality of cameras, for example, the plurality of cameras may be driven selectively on the basis of a field of view. However, such a method may cause a time delay in image-processing in the process of selectively turning on/off the plurality of cameras, and the time delay may affect the photographed images, thereby causing interruption in displaying the images.

Solution to Problem

A method for processing multiple images according to embodiments of the disclosure may include: acquiring multiple images using a plurality of cameras; extracting image information on each of the acquired multiple images; performing preprocessing for calculating at least one piece of auto focus (AF) data, auto exposure (AE) data, and auto white balance (AWB) data of the multiple images on the basis of the extracted image information and generating parameters corresponding to the respective images; selecting one or more images required according to a zoom magnification from among the acquired multiple images; and performing image-processing by applying parameters corresponding to the one or more selected images.

An electronic device according to embodiments of the disclosure may include: a plurality of cameras configured to acquire multiple images; an image information extracting device configured to extract image information on each of the acquired multiple images; an image selector configured to perform preprocessing for calculating at least one piece of auto focus (AF) data, auto exposure (AE) data, and auto white balance (AWB) data of the multiple images on the basis of the extracted image information, generate parameters corresponding to the respective images, and select one or more images required according to a zoom magnification from among the acquired multiple images; and an image processor configured to perform image-processing by applying parameters corresponding to the one or more selected images.

An electronic device according to embodiments of the disclosure may include: a first camera; a second camera; a processor; and a display operably connected to the processor, wherein the processor is configured to: acquire a first image by means of the first camera and a second image by means of the second camera; determine parameters for processing the first or second image at least on the basis of the first image and the second image; correct the first and second images using a first image-processing method related to the parameters; if an input in relation to the first image and the second image satisfies a specified condition, process the corrected first image using a second image-processing method related to the parameters and display the processed first image on the display; and if the input satisfies another specified condition, process the corrected second image using the second image-processing method and display the processed second image on the display.

Advantageous Effects of Invention

According to embodiments of the disclosure, since an image having a desired field of view is selected from, for example, the images acquired by a plurality of cameras and is processed or stored, it is possible to reduce power consumption and memory consumption.

According to embodiments of the disclosure, it is possible to provide images without a delay time or interruption, for example, during the switching operation between a plurality of cameras.

According to embodiments of the disclosure, for example, an image to be displayed can be corrected in consideration of parameters related to image-processing of the image that is being displayed. In addition, it is possible to eliminate interruption of the images when, for example, images acquired by a plurality of cameras are synthesized and displayed.

MODE FOR THE INVENTION

Figure 1:
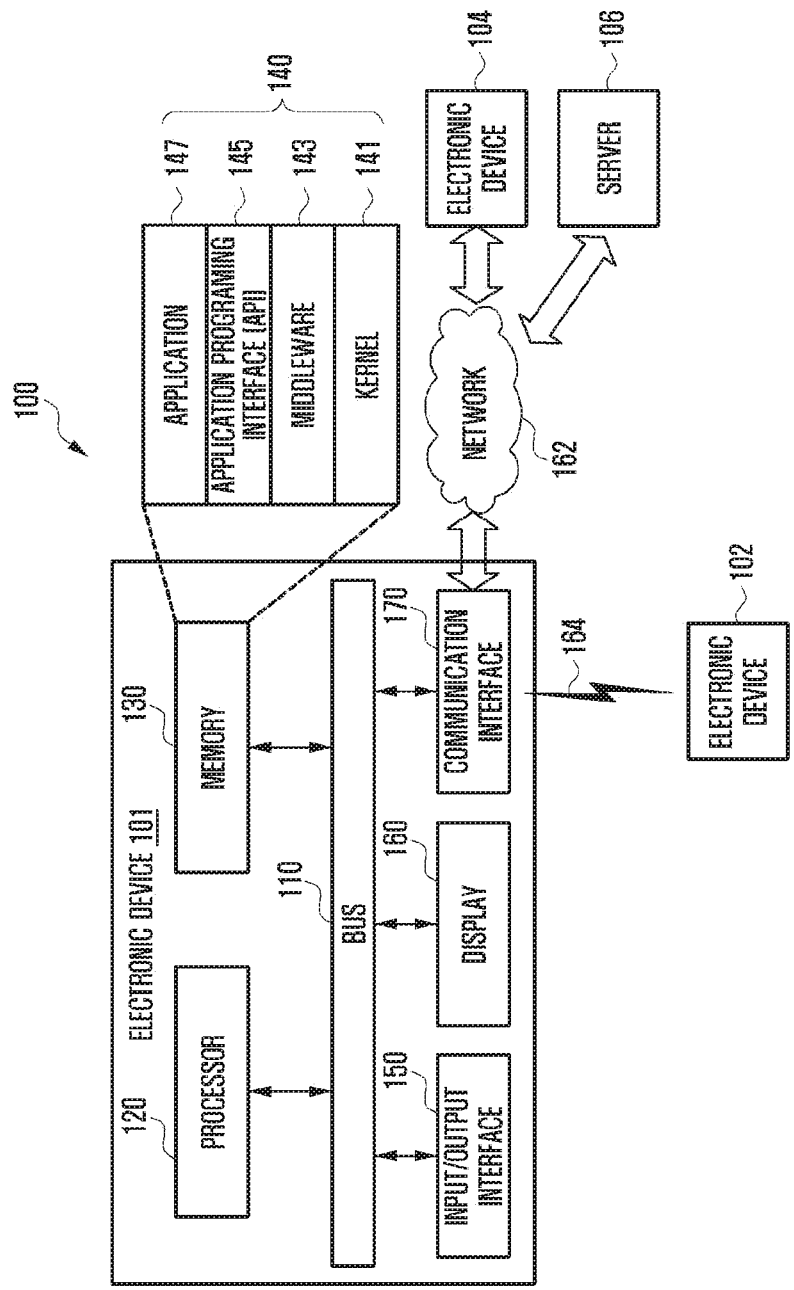
FIG. 1 is a block diagram of an electronic device in a network environment according to embodiments.

Hereinafter, various embodiments of the present disclosure may be described with reference to accompanying drawings. Accordingly, those of ordinary skill in the art will recognize that modification, equivalent, and/or alternative on the various embodiments described herein can be variously made without departing from the scope and spirit of the present disclosure. With regard to description of drawings, similar elements may be marked by similar reference numerals. The terms of a singular form may include plural forms unless otherwise specified. In this disclosure, the expressions "A or B", "at least one of A or/and B", or "one or more of A or/and B", and the like may include any and all combinations of one or more of the associated listed items. The terms, such as "first", "second", and the like may be used to refer to various elements regardless of the order and/or the priority and to distinguish the relevant elements from other elements, but do not limit the elements. When an element (e.g., a first element) is referred to as being "(operatively or communicatively) coupled with/to" or "connected to" another element (e.g., a second element), the element may be directly coupled with/to or connected to the other element or an intervening element (e.g., a third element) may be present.

According to the situation, the expression "configured to" used in this disclosure may be used as, for example, the expression "suitable for", "having the capacity to", "adapted to", "made to", "capable of", or "designed to" in hardware or software. The expression "a device configured to" may mean that the device is "capable of" operating together with another device or other components. For example, a "processor configured to (or set to) perform A, B, and C" may mean a dedicated processor (e.g., an embedded processor) for performing a corresponding operation or a generic-purpose processor (e.g., a central processing unit (CPU) or an application processor) which performs corresponding operations by executing one or more software programs which are stored in a memory device.

An electronic device according to various embodiments of this disclosure may include at least one of, for example, smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, medical devices, cameras, or wearable devices. According to various embodiments, the wearable device may include at least one of an accessory type (e.g., watches, rings, bracelets, anklets, necklaces, glasses, contact lens, or head-mounted-devices (HMDs), a fabric or garment-integrated type (e.g., an electronic apparel), a body-attached type (e.g., a skin pad or tattoos), or a bio-implantable type (e.g., an implantable circuit). According to various embodiments, the electronic device may include at least one of, for example, televisions (TVs), digital versatile disc (DVD) players, audios, refrigerators, air conditioners, cleaners, ovens, microwave ovens, washing machines, air cleaners, set-top boxes, home automation control panels, security control panels, media boxes (e.g., Samsung HomeSync™, Apple TV™, or Google TV™), game consoles (e.g., Xbox™ or PlayStation™), electronic dictionaries, electronic keys, camcorders, electronic picture frames, and the like.

According to another embodiment, an electronic device may include at least one of various medical devices (e.g., various portable medical measurement devices (e.g., a blood glucose monitoring device, a heartbeat measuring device, a blood pressure measuring device, a body temperature measuring device, and the like), a magnetic resonance angiography (MRA), a magnetic resonance imaging (MRI), a computed tomography (CT), scanners, and ultrasonic devices), navigation devices, Global Navigation Satellite System (GNSS), event data recorders (EDRs), flight data recorders (FDRs), vehicle infotainment devices, electronic equipment for vessels (e.g., navigation systems and gyrocompasses), avionics, security devices, head units for vehicles, industrial or home robots, drones, automatic teller's machines (ATMs), points of sales (POSs) of stores, or internet of things (e.g., light bulbs, various sensors, sprinkler devices, fire alarms, thermostats, street lamps, toasters, exercise equipment, hot water tanks, heaters, boilers, and the like). According to an embodiment, the electronic device may include at least one of parts of furniture or buildings/structures, electronic boards, electronic signature receiving devices, projectors, or various measuring instruments (e.g., water meters, electricity meters, gas meters, or wave meters, and the like). According to various embodiments, the electronic device may be a flexible electronic device or a combination of two or more above-described devices. Furthermore, an electronic device according to an embodiment of this disclosure may not be limited to the above-described electronic devices. In this disclosure, the term "user" may refer to a person who uses an electronic device or may refer to a device (e.g., an artificial intelligence electronic device) that uses the electronic device.

In the following, in order to conveniently explain the present disclosure, the various embodiments of the present disclosure are explained with the electronic device being a mobile terminal (e.g., smartphone). In addition, the embodiments are explained with the electronic device including a plurality of cameras. However, the various embodiments of the present disclosure are not limited to the disclosed embodiments.

Methods of acquiring and processing images disclosed in this document may include at least some of the various image standards. For example, the dual-image standard may be based on the Exif Ver. 2.3 standard, which was established/revised by the Camera & Imaging Product Association (CIPA) International Standards Organization. According to the dual-image standard, it is possible to efficiently process/control the dual image while ensuring basic backward compatibility in reproduction terminals such as a smart phone, a camera, or a TV set.

Dual-image and related metadata standards may perform allocation using the APPn marker code, which allows basic JPEG extension. For example, images acquired by a plurality of image sensors may be stored in a memory as a single file. Dual metadata information or the like may be defined declaring the APP1 maker code, and dual-image information may be allocated in the same file through separate spaces as a hierarchical structure using various zoom changes. This format enables efficient control of various dual-image usage scenarios, and is compatible with lower models, thereby providing trouble-free reproduction. A user may be provided with these effects through various user interfaces (UIs) of the electronic devices.

In order to utilize dual-image scenario functions in the electronic devices, a variety of dual parameter information, such as zoom magnification, offset setting, and the like, may be required. The dual parameter information or the like can be expressed in various forms, such as integers, floating point values, ASCII, or the like, and can be extended to a tagged image file format (TIFF), an extensible metadata platform (XMP), or the like as a technique for exchanging data.

A large amount of memory capacity may be consumed in order to, for example, independently store images acquired by a plurality of image sensors. Therefore, codecs suitable for usage scenarios using the dual image (Tele/Wide or the like) may be applied. For example, the dual image in the same field of view may contain many visual redundancy components based on zoom characteristics. Therefore, it is possible to configure low entropy data by applying a technique for eliminating the visual redundancy based on the zoom characteristics, thereby reducing the amount of data information. Examples of data compression techniques may include differential pulse coded modulation (DPCM), motion estimation (ME)/motion compensation (MC), or the like, and may obtain a memory space of 30% to 40% more than the independent dual-image storage method.

Referring to FIG. 1, according to various embodiments, an electronic device 101 in a network environment is described.

The electronic device 101 may include a bus 110, a processor 120, a memory 130, an input/output interface 150, a display 160, and a communication interface 170. According to an embodiment, the electronic device 101 may not include at least one of the above-described elements or may further include other element(s). The bus 110 may interconnect the above-described elements 110 to 170 and may include a circuit for conveying communications (e.g., a control message and/or data) among the above-described elements. The processor 120 may include one or more of a central processing unit (CPU), an application processor (AP), or a communication processor (CP). For example, the processor 120 may perform an arithmetic operation or data processing associated with control and/or communication of at least other elements of the electronic device 101.

The memory 130 may include a volatile and/or nonvolatile memory. For example, the memory 130 may store instructions or data associated with at least one other element(s) of the electronic device 101. According to an embodiment, the memory 130 may store software and/or a program 140. The program 140 may include, for example, a kernel 141, a middleware 143, an application programming interface (API) 145, and/or an application program (or "application") 147. At least a part of the kernel 141, the middleware 143, or the API 145 may be referred to as an "operating system (OS)". For example, the kernel 141 may control or manage system resources (e.g., the bus 110, the processor 120, the memory 130, and the like) that are used to execute operations or functions of other programs (e.g., the middleware 143, the API 145, and the application program 147). Furthermore, the kernel 141 may provide an interface that allows the middleware 143, the API 145, or the application program 147 to access discrete elements of the electronic device 101 so as to control or manage system resources.

The middleware 143 may perform, for example, a mediation role such that the API 145 or the application program 147 communicates with the kernel 141 to exchange data. Furthermore, the middleware 143 may process one or more task requests received from the application program 147 according to a priority. For example, the middleware 143 may assign the priority, which makes it possible to use a system resource (e.g., the bus 110, the processor 120, the memory 130, or the like) of the electronic device 101, to at least one of the application program 147 and may process the one or more task requests. The API 145 may be an interface through which the application program 147 controls a function provided by the kernel 141 or the middleware 143, and may include, for example, at least one interface or function (e.g., a command or an instruction) for a file control, a window control, image processing, a character control, or the like. The input/output interface 150 may transmit an instruction or data input from a user or another external device, to other element(s) of the electronic device 101 or may output an instruction or data, received from other element(s) of the electronic device 101, to a user or another external device.

The display 160 may include, for example, a liquid crystal display (LCD), a light-emitting diode (LED) display, an organic LED (OLED) display, a microelectromechanical systems (MEMS) display, or an electronic paper display. The display 160 may display, for example, various contents (e.g., a text, an image, a video, an icon, a symbol, and the like) to a user. The display 160 may include a touch screen and may receive, for example, a touch, gesture, proximity, or hovering input using an electronic pen or a part of a user's body. For example, the communication interface 170 may establish communication between the electronic device 101 and an external device (e.g., the first electronic device 102, the second electronic device 104, or the server 106). For example, the communication interface 170 may be connected to the network 162 over wireless communication or wired communication to communicate with the external device (e.g., the second electronic device 104 or the server 106).

For example, the wireless communication may include cellular communication using at least one of long-term evolution (LTE), LTE Advanced (LTE-A), Code Division Multiple Access (CDMA), Wideband CDMA (WCDMA), Universal Mobile Telecommunications System (UMTS), Wireless Broadband (WiBro), Global System for Mobile Communications (GSM), or the like. The wireless communication may include at least one of wireless fidelity (Wi-Fi), Bluetooth, Bluetooth low energy (BLE), Zigbee, near field communication (NFC), magnetic stripe transmission (MST), radio frequency (RF), a body area network, or the like. According to an embodiment, the wireless communication may include GNSS. The GNSS may be one of, for example, a global positioning system (GPS), a global navigation satellite system (Glonass), a Beidou navigation satellite system (hereinafter referred to as "Beidou"), or an European global satellite-based navigation system (hereinafter referred to as "Galileo"). Hereinafter, in this disclosure, "GPS" and "GNSS" may be interchangeably used. The wired communication may include at least one of, for example, a universal serial bus (USB), a high definition multimedia interface (HDMI), a recommended standard-232 (RS-232), power line communication, a plain old telephone service (POTS), or the like. The network 162 may include at least one of telecommunications networks, for example, a computer network (e.g., LAN or WAN), an Internet, or a telephone network.

Each of the first and second external electronic devices 102 and 104 may be a device of which the type is different from or the same as that of the electronic device 101. According to various embodiments, all or a portion of operations that the electronic device 101 will perform may be executed by another or plural electronic devices (e.g., the first electronic device 102, the second electronic device 104 or the server 106). According to an embodiment, in the case where the electronic device 101 executes any function or service automatically or in response to a request, the electronic device 101 may not perform the function or the service internally, but, alternatively additionally, it may request at least a portion of a function associated with the electronic device 101 at other electronic device (e.g., the electronic device 102 or 104 or the server 106). The other electronic device (e.g., the electronic device 102 or 104 or the server 106) may execute the requested function or additional function and may transmit the execution result to the electronic device 101. The electronic device 101 may provide the requested function or service using the received result or may additionally process the received result to provide the requested function or service. To this end, for example, cloud computing, distributed computing, or client-server computing may be used.

Figure 2:
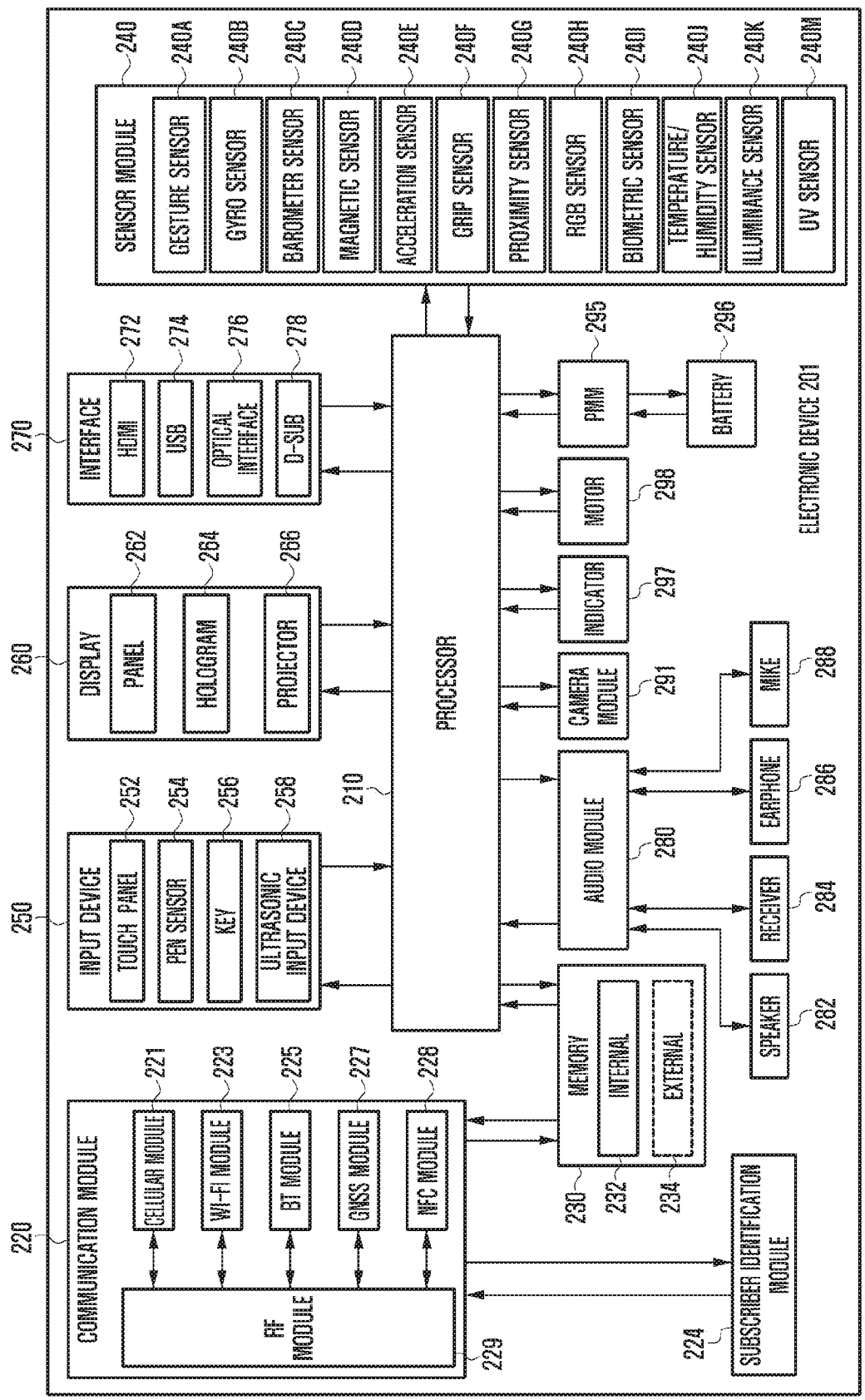
FIG. 2 is a block diagram of an electronic device according to embodiments.

FIG. 2 illustrates a block diagram of an electronic device, according to various embodiments.

FIG. 2 illustrates a block diagram of an electronic device, according to various embodiments. An electronic device 201 may include, for example, all or a part of the electronic device 101 illustrated in FIG. 1. The electronic device 201 may include one or more processors (e.g., an application processor (AP)) 210, a communication module 220, a subscriber identification module 224, a memory 230, a sensor module 240, an input device 250, a display 260, an interface 270, an audio module 280, a camera module 291, a power management module 295, a battery 296, an indicator 297, and a motor 298. For example, the processor 210 may be implemented with a System on Chip (SoC). According to an embodiment, the processor 210 may further include a graphic processing unit (GPU) and/or an image signal processor. The processor 210 may include at least a part (e.g., a cellular module 221) of elements illustrated in FIG. 2. The processor 210 may load an instruction or data, which is received from at least one of other elements (e.g., a nonvolatile memory), into a volatile memory and process the loaded instruction or data. The processor 210 may store result data in the nonvolatile memory.

The communication module 220 may be configured the same as or similar to the communication interface 170 of FIG. 1. The communication module 220 may include the cellular module 221, a Wi-Fi module 223, a Bluetooth (BT) module 225, a GNSS module 227, a near field communication (NFC) module 228, and a radio frequency (RF) module 229. The cellular module 221 may provide, for example, voice communication, video communication, a character service, an Internet service, or the like over a communication network. According to an embodiment, the cellular module 221 may perform discrimination and authentication of the electronic device 201 within a communication network by using the subscriber identification module (e.g., a SIM card) 224. According to an embodiment, the cellular module 221 may perform at least a portion of functions that the processor 210 provides. According to an embodiment, the cellular module 221 may include a communication processor (CP). According to an embodiment, at least a part (e.g., two or more) of the cellular module 221, the Wi-Fi module 223, the BT module 225, the GNSS module 227, or the NFC module 228 may be included within one Integrated Circuit (IC) or an IC package. For example, the RF module 229 may transmit and receive a communication signal (e.g., an RF signal). For example, the RF module 229 may include a transceiver, a power amplifier module (PAM), a frequency filter, a low noise amplifier (LNA), an antenna, or the like. According to another embodiment, at least one of the cellular module 221, the Wi-Fi module 223, the BT module 225, the GNSS module 227, or the NFC module 228 may transmit and receive an RF signal through a separate RF module. The subscriber identification module 224 may include, for example, a card and/or embedded SIM that includes a subscriber identification module and may include unique identify information (e.g., integrated circuit card identifier (ICCID)) or subscriber information (e.g., international mobile subscriber identity (IMSI)).

The memory 230 (e.g., the memory 130) may include an internal memory 232 or an external memory 234. For example, the internal memory 232 may include at least one of a volatile memory (e.g., a dynamic random access memory (DRAM), a static RAM (SRAM), a synchronous DRAM (SDRAM), or the like), a nonvolatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory, a hard drive, or a solid state drive (SSD). The external memory 234 may include a flash drive such as compact flash (CF), secure digital (SD), micro secure digital (Micro-SD), mini secure digital (Mini-SD), extreme digital (xD), a multimedia card (MMC), a memory stick, or the like. The external memory 234 may be operatively and/or physically connected to the electronic device 201 through various interfaces.

The sensor module 240 may measure, for example, a physical quantity or may detect an operation state of the electronic device 201. The sensor module 240 may convert the measured or detected information to an electric signal. For example, the sensor module 240 may include at least one of a gesture sensor 240A, a gyro sensor 240B, a barometric pressure sensor 240C, a magnetic sensor 240D, an acceleration sensor 240E, a grip sensor 240F, the proximity sensor 240G, a color sensor 240H (e.g., red, green, blue (RGB) sensor), a biometric sensor 240I, a temperature/humidity sensor 240J, an illuminance sensor 240K, or an UV sensor 240M. Although not illustrated, additionally or generally, the sensor module 240 may further include, for example, an E-nose sensor, an electromyography (EMG) sensor, an electroencephalogram (EEG) sensor, an electrocardiogram (ECG) sensor, an infrared (IR) sensor, an iris sensor, and/or a fingerprint sensor. The sensor module 240 may further include a control circuit for controlling at least one or more sensors included therein. According to an embodiment, the electronic device 201 may further include a processor that is a part of the processor 210 or independent of the processor 210 and is configured to control the sensor module 240. The processor may control the sensor module 240 while the processor 210 remains at a sleep state.

The input device 250 may include, for example, a touch panel 252, a (digital) pen sensor 254, a key 256, or an ultrasonic input unit 258. For example, the touch panel 252 may use at least one of capacitive, resistive, infrared and ultrasonic detecting methods. Also, the touch panel 252 may further include a control circuit. The touch panel 252 may further include a tactile layer to provide a tactile reaction to a user. The (digital) pen sensor 254 may be, for example, a part of a touch panel or may include an additional sheet for recognition. The key 256 may include, for example, a physical button, an optical key, or a keypad. The ultrasonic input device 258 may detect (or sense) an ultrasonic signal, which is generated from an input device, through a microphone (e.g., a microphone 288) and may check data corresponding to the detected ultrasonic signal.

The display 260 (e.g., the display 160) may include a panel 262, a hologram device 264, a projector 266, and/or a control circuit for controlling the panel 262, the hologram device 264, or the projector 266. The panel 262 may be implemented, for example, to be flexible, transparent or wearable. The panel 262 and the touch panel 252 may be integrated into a single module. According to an embodiment, the panel 262 may include a pressure sensor (or force sensor) that measures the intensity of touch pressure by a user. The pressure sensor may be implemented integrally with the touch panel 252, or may be implemented as at least one sensor separately from the touch panel 252. The hologram device 264 may display a stereoscopic image in a space using a light interference phenomenon. The projector 266 may project light onto a screen so as to display an image. For example, the screen may be arranged in the inside or the outside of the electronic device 201. The interface 270 may include, for example, a high-definition multimedia interface (HDMI) 272, a universal serial bus (USB) 274, an optical interface 276, or a D-subminiature (D-sub) 278. The interface 270 may be included, for example, in the communication interface 170 illustrated in FIG. 1. Additionally or generally, the interface 270 may include, for example, a mobile high definition link (MHL) interface, a SD card/multi-media card (MMC) interface, or an infrared data association (IrDA) standard interface.

The audio module 280 may convert a sound and an electric signal in dual directions. At least a part of the audio module 280 may be included, for example, in the input/output interface 150 illustrated in FIG. 1. The audio module 280 may process, for example, sound information that is input or output through a speaker 282, a receiver 284, an earphone 286, or the microphone 288.

For example, the camera module 291 may shoot a still image or a video. According to an embodiment, the camera module 291 may include at least one or more image sensors (e.g., a front sensor or a rear sensor), a lens, an image signal processor (ISP), or a flash (e.g., an LED or a xenon lamp). The camera module 291 of the various embodiments of the present disclosure can include a plurality of sensors that can recognize an object that is external to the electronic device 201.

The power management module 295 may manage, for example, power of the electronic device 201. According to an embodiment, a power management integrated circuit (PMIC), a charger IC, or a battery or fuel gauge may be included in the power management module 295. The PMIC may have a wired charging method and/or a wireless charging method. The wireless charging method may include, for example, a magnetic resonance method, a magnetic induction method or an electromagnetic method and may further include an additional circuit, for example, a coil loop, a resonant circuit, a rectifier, or the like. The battery gauge may measure, for example, a remaining capacity of the battery 296 and a voltage, current or temperature thereof while the battery is charged. The battery 296 may include, for example, a rechargeable battery and/or a solar battery.

The indicator 297 may display a specific state of the electronic device 201 or a part thereof (e.g., the processor 210), such as a booting state, a message state, a charging state, and the like. The motor 298 may convert an electrical signal into a mechanical vibration and may generate the following effects: vibration, haptic, and the like. The electronic device 201 may include a processing device (e.g., a GPU) for supporting a mobile TV. The processing device for supporting the mobile TV may process media data according to the standards of digital multimedia broadcasting (DMB), digital video broadcasting (DVB), MediaFLO™, or the like. Each of the above-mentioned elements of the electronic device according to various embodiments of the present disclosure may be configured with one or more components, and the names of the elements may be changed according to the type of the electronic device. In various embodiments, some elements of the electronic device (e.g., the electronic device 201) may be omitted or other additional elements may be added. Furthermore, some of the elements of the electronic device may be combined with each other so as to form one entity, so that the functions of the elements may be performed in the same manner as before the combination.

Figure 3:
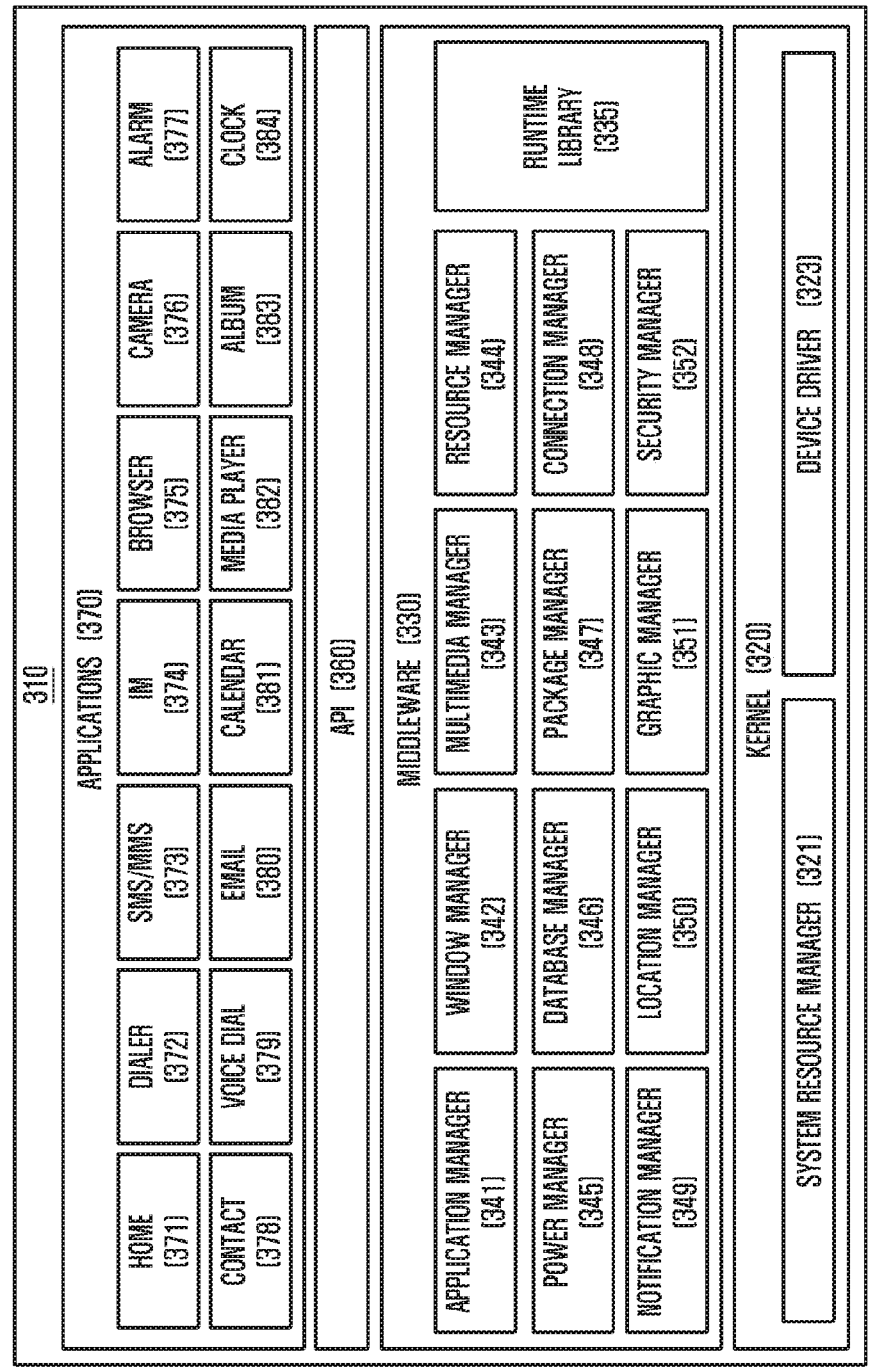
FIG. 3 is a block diagram of a program module according to embodiments.

FIG. 3 illustrates a block diagram of a program module, according to various embodiments.

According to an embodiment, a program module 310 (e.g., the program 140) may include an operating system (OS) to control resources associated with an electronic device (e.g., the electronic device 101), and/or diverse applications (e.g., the application program 147) driven on the OS. The OS may be, for example, Android™, iOS™, Windows™, Symbian™, Tizen™, or Bada™. The program module 310 may include a kernel 320 (e.g., the kernel 141), a middleware 330 (e.g., the middleware 143), an application programming interface (API) 360 (e.g., the API 145), and/or an application 370 (e.g., the application program 147). At least a portion of the program module 310 may be preloaded on an electronic device or may be downloadable from an external electronic device (e.g., the first electronic device 102, the second electronic device 104, the server 106, or the like).

The kernel 320 (e.g., the kernel 141) may include, for example, a system resource manager 321 or a device driver 323. The system resource manager 321 may control, allocate, or retrieve system resources. According to an embodiment, the system resource manager 321 may include a process managing unit, a memory managing unit, a file system managing unit, or the like. The device driver 323 may include, for example, a display driver, a camera driver, a Bluetooth driver, a shared memory driver, a USB driver, a keypad driver, a Wi-Fi driver, an audio driver, or an inter-process communication (IPC) driver. The middleware 330 may provide, for example, a function that the application 370 needs in common, or may provide diverse functions to the application 370 through the API 360 to allow the application 370 to efficiently use limited system resources of the electronic device. According to an embodiment, the middleware 330 may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, or a security manager 352.

The runtime library 335 may include, for example, a library module that is used by a compiler to add a new function through a programming language while the application 370 is being executed. The runtime library 335 may perform input/output management, memory management, or capacities about arithmetic functions. The application manager 341 may manage, for example, a life cycle of at least one application of the application 370. The window manager 342 may manage a graphic user interface (GUI) resource that is used in a screen. The multimedia manager 343 may identify a format necessary for playing diverse media files, and may perform encoding or decoding of media files by using a codec suitable for the format. The resource manager 344 may manage resources such as a memory space or source code of the application 370. The power manager 345 may manage a battery or power, and may provide power information for an operation of an electronic device. According to an embodiment, the power manager 345 may operate with a basic input/output system (BIOS). The database manager 346 may generate, search for, or modify database that is to be used in the application 370. The package manager 347 may install or update an application that is distributed in the form of package file.

The connectivity manager 348 may manage, for example, wireless connection. The notification manager 349 may provide an event, for example, arrival message, appointment, or proximity notification to a user. For example, the location manager 350 may manage location information about an electronic device. The graphic manager 351 may manage a graphic effect that is provided to a user, or manage a user interface relevant thereto. The security manager 352 may provide, for example, system security or user authentication. According to an embodiment, the middleware 330 may include a telephony manager for managing a voice or video call function of the electronic device or a middleware module that combines diverse functions of the above-described elements. According to an embodiment, the middleware 330 may provide a module specialized to each OS kind to provide differentiated functions. Additionally, the middleware 330 may dynamically remove a part of the preexisting elements or may add new elements thereto. The API 360 may be, for example, a set of programming functions and may be provided with a configuration that is variable depending on an OS. For example, in the case where an OS is the android or the iOS, it may provide one API set per platform. In the case where an OS is the tizen, it may provide two or more API sets per platform.

The application 370 may include, for example, applications such as a home 371, a dialer 372, an SMS/MMS 373, an instant message (IM) 374, a browser 375, a camera 376, an alarm 377, a contact 378, a voice dial 379, an e-mail 380, a calendar 381, a media player 382, an album 383, a watch 384, health care (e.g., measuring an exercise quantity, blood sugar, or the like) or offering of environment information (e.g., information of barometric pressure, humidity, temperature, or the like). According to an embodiment, the application 370 may include an information exchanging application to support information exchange between an electronic device and an external electronic device. The information exchanging application may include, for example, a notification relay application for transmitting specific information to an external electronic device, or a device management application for managing the external electronic device. For example, the notification relay application may include a function of transmitting notification information, which arise from other applications, to an external electronic device or may receive, for example, notification information from an external electronic device and provide the notification information to a user. The device management application may install, delete, or update for example, a function (e.g., turn-on/turn-off of an external electronic device itself (or a part of components) or adjustment of brightness (or resolution) of a display) of the external electronic device which communicates with the electronic device, and an application running in the external electronic device. According to an embodiment, the application 370 may include an application (e.g., a health care application of a mobile medical device) that is assigned in accordance with an attribute of an external electronic device. According to an embodiment, the application 370 may include an application that is received from an external electronic device. At least a portion of the program module 310 may be implemented by software, firmware, hardware (e.g., the processor 210), or a combination (e.g., execution) of two or more thereof, and may include modules, programs, routines, sets of instructions, processes, or the like for performing one or more functions.

Figure 4:
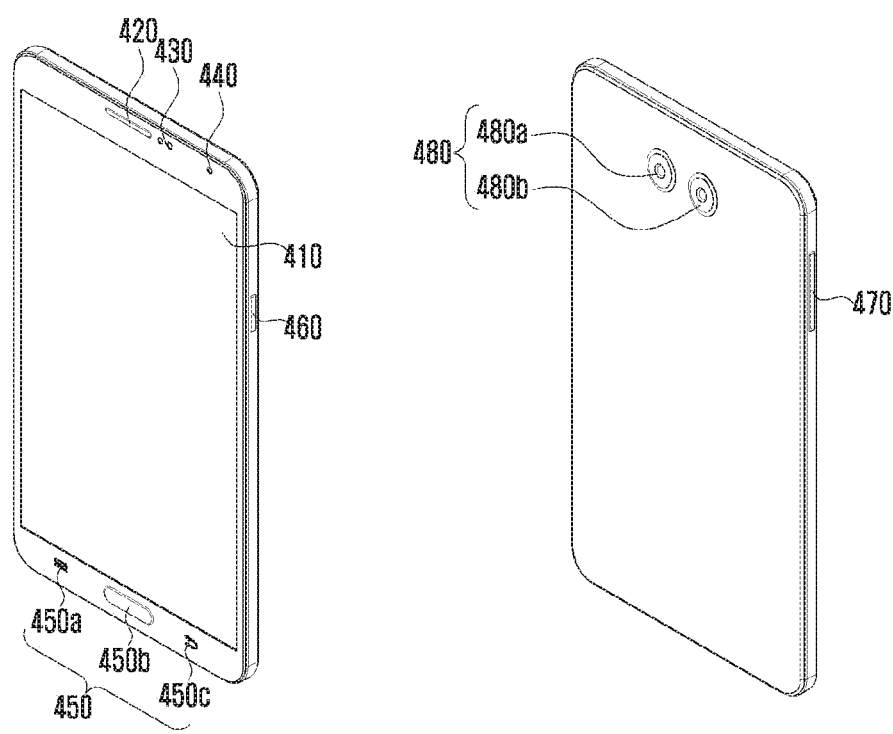
FIG. 4 is view illustrating a front surface and a back surface of an electronic device according to embodiments of the disclosure.

FIG. 4 is view illustrating a front surface and a back surface of an electronic device according to embodiments of the disclosure.

Referring to FIG. 4, an electronic device 201 according to an embodiment of the disclosure may include a display 410 positioned on a front surface thereof, a speaker (e.g., a receiver 420), an illuminance sensor 430, and a front camera 440, which are positioned at the upper portion of the display 410, and a plurality of keys 450 positioned at the lower portion of the display 410. For example, the plurality of keys 450 may include a menu key 450a, a home key 450b, and a cancellation key 450c.

A power key 460 and a volume key 470 may be positioned on a side surface of the electronic device 201. In addition, a rear camera 480 may be positioned on the rear (or back) surface of the electronic device 201. For example, at least a portion of the rear camera 480 may be mounted in a housing of the electronic device 201. The rear camera 480 may include dual camera 480a and 480b. One of the dual cameras 480a and 480b may be configured to include a wide angle lens and the other may be configured to include a telephoto lens, or both of the dual cameras 480a and 480b may be configured to include the same lens. In some embodiments, one of the dual cameras 480a and 480b may be configured to include an RGB lens, and the other may be configured to include a monochrome lens. The dual cameras 480a and 480b may provide a more accurate contrast value or freer focus and depth adjustment than a single camera.

The electronic device 201 shown in FIG. 4 is only an example, and the embodiment of the disclosure is not limited thereto. For example, although the electronic device 201 is shown as a bar type in FIG. 4, the electronic device 201 may be a folder type, a slide type, or a flexible type.

Although the rear camera 480 of the electronic device 201 includes a dual camera in FIG. 4, the rear camera 480 of the electronic device 201 according to another embodiment of the disclosure may include three or more cameras. In addition, the front camera 440 of the electronic device 201 may include a plurality of cameras.

Although the electronic device 201 is shown as a portable terminal in FIG. 4, the electronic device 201 according to embodiments of the disclosure may be any electronic device that can employ a camera.

Figure 5:
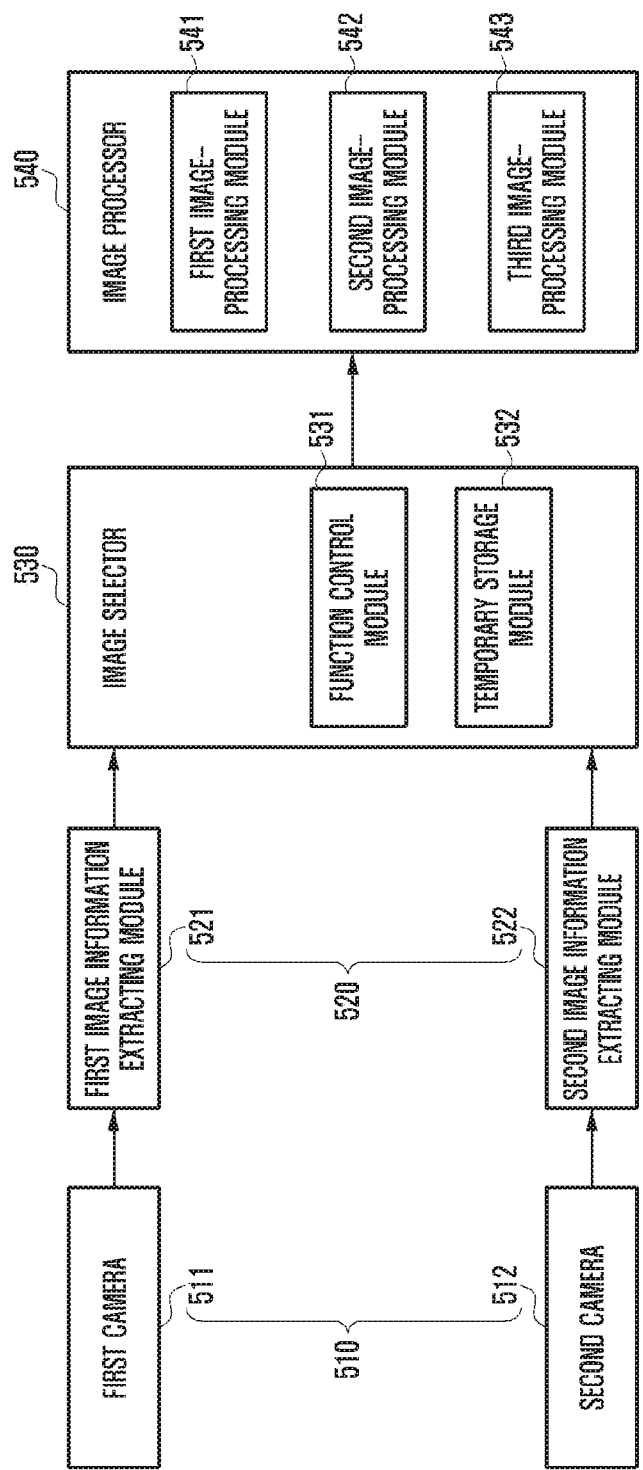
FIG. 5 is a structural diagram illustrating an electronic device including a plurality of cameras according to embodiments of the disclosure.

FIG. 5 is a structural diagram illustrating an electronic device including a plurality of cameras according to embodiments of the disclosure.

According to embodiments, the electronic device 201 may include a plurality of cameras 510, image information extracting modules 520, an image selector 530, and an image processor 540. It should be noted that the embodiments of the disclosure need not necessarily include all of the above components, and that in some embodiments the electronic device 201 may exclude at least one of the components or may further include other components. In addition, although the image information extracting modules 520, the image selector 530, and the image processor 540 are illustrated as separate components in FIG. 5, they may be configured as a single component (e.g., the processor 210) performing respective operations thereof.

According to embodiments, the plurality of cameras 510 (e.g., the camera module 291) may include cameras having different characteristics (e.g., brightness, focal length, shutter speed, magnification, resolution, field of view, and the like). For example, the first camera 511 and the second camera 512 may include cameras having different focal lengths and/or different fields of view.

According to an embodiment, the plurality of cameras 510 may be a dual camera. The dual camera may include a first camera 511 including a wide angle lens and a second camera 512 including a telephoto lens. For example, the first camera 511 may be configured to focus on the subject, and the second camera 512 may be configured to focus on the background of the subject. Although FIG. 5 illustrates an example in which the plurality of cameras 510 include a dual camera, but the plurality of cameras 510 may include three or more cameras.

According to embodiments, the image information extracting modules 520 (e.g., the processor 210) may extract image information on each of the images acquired from the plurality of cameras 510. The image information extracting module may extract image information from the images photographed by cameras having different focal lengths and/or different fields of view. The image information may include, for example, phase difference information, an edge value, an RGB channel value, and the like. The phase difference information, the edge value, and the RGB channel value included in the image information may be used to generate parameters for synthesizing multiple images. In some embodiments, data for performing RGB histogram and auto focus (AF) may be calculated using the extracted image information. Although FIG. 5 shows that the electronic device 201 includes image information extracting modules (e.g., a first image information extracting module 521 and a second image information extracting module 522) corresponding to the respective cameras, the electronic device may be configured to include a single image information extracting module 520, and the single image information extracting module 520 may receive images from the respective cameras 510 and may extract image information.

According to embodiments, the image selector 530 (e.g., the processor 210) may include a function control module 531 and a temporary storage module 532. The function control module 531 may perform preprocessing on the multiple images on the basis of the extracted image information, and may generate parameters corresponding to the respective images. The preprocessing of images may include, for example, performing operations of auto white balance (AWB), auto exposure (AE), and auto focus (AF). The electronic device 201 may perform the above operations, thereby calculating AF data for focus adjustment, AE data for exposure adjustment, AWB data for white balance adjustment. The parameters may be variables used to perform a variety of image-processing such as zoom adjustment, offset setting, or the like. In addition, the parameters may be used to perform synchronization between multiple images when the multiple images are synthesized.

In addition, the function control module 531 may select one or more images required according to a zoom magnification from among, for example, the acquired multiple images. For example, if the zoom magnification is changed, and if one or more images suitable for the changed zoom magnification are selected by the function control module, the temporary storage module 532 may perform control such that the one or more selected images are temporarily stored in a memory and/or a buffer. Although the image selector is illustrated as including the function control module and the temporary storage module in FIG. 5, the electronic device 201 may be configured to include a function control module 531 and a temporary storage module 532, which are separately provided.

According to an embodiment, if one or more images to be displayed on the screen are selected from among the multiple images, the electronic device 201 may change an operation related to image acquisition. For example, if an image acquired using the first camera 511 is selected, the electronic device 201 may change the frame rate of the second camera 512 (e.g., the electronic device 201 may set the frame rate of second camera 512 to be lower than the frame rate of first camera 511). As another example, if an image acquired using the second camera 512 is selected, the electronic device 201 may change the frame rate of the first camera 511 (e.g., the electronic device 201 may set the frame rate of the first camera 511 to be lower than the frame rate of the second camera 512). As another example, if an image acquired using the first camera 511 is selected, the electronic device 201 may deactivate the second camera 512 (e.g., the second camera 512 may operate in a low-power mode). As another example, if an image acquired using the second camera 512 is selected, the electronic device 201 may deactivate the first camera 511 (e.g., the first camera 511 may operate in a low-power mode).

According to embodiments, the image processor 540 (e.g., the processor 210) may process one or more images selected by the image selector 530. The image processor 540 may include a first image-processing module 541, a second image-processing module 542, and a third image-processing module 543. Although the first image-processing module 541, the second image-processing module 542, and the third image-processing module 543 are shown separately in FIG. 5, a single component (e.g., the processor 210) may be configured to process respective operations thereof.

The first image-processing module 541 may be configured to perform first image-processing in relation to, for example, the correction of one or more images selected by the image selector 530. The images photographed by the cameras include a variety of information, but components of a brightness signal and/or a color signal may be biased or distorted depending on objects, the performance of the camera, or shooting conditions. Therefore, the first image-processing may be intended to correct the brightness signal and/or a color signal. The first image-processing may include, for example, lens shading compensation, black level correction, and defective pixel correction.

The second image-processing module 542 may be configured to perform second image-processing in order to improve, for example, resolution and quality of the image that has been executed with the first image-processing. The second image-processing may include, for example, demosaicking to more accurately represent colors of an image, denoising to remove noise, gamma correction, and sharpening to emphasize details of an image.

If multiple images are selected, the third image-processing module 543 may be configured to perform third image-processing to compensate for the difference in the field of view between the multiple images in order to perform synthesis of the multiple images. Although FIG. 5 shows that the image processor includes the first image-processing module 541, the second image-processing module 542, and the third image-processing module 543, the electronic device may include the first image-processing module 541, the second image-processing module 542, and the third image-processing module 543 as separate components. In addition, although FIG. 5 shows that one image-processing module processes an image acquired from each camera, the electronic device 201 may be configured to include a first image-processing module 541 and a second image-processing module 542 corresponding to the respective cameras.

An electronic device according to embodiments of the disclosure may include: a plurality of cameras configured to acquire multiple images; an image information extracting device configured to extract image information on each of the acquired multiple images; an image selector configured to perform preprocessing for calculating at least one piece of auto focus (AF) data, auto exposure (AE) data, and auto white balance (AWB) data of the multiple images on the basis of the extracted image information, generate parameters corresponding to the respective images, and select one or more images required according to a zoom magnification from among the acquired multiple images; and an image processor configured to perform image-processing by applying parameters corresponding to the one or more selected images.

The image information of the electronic device according to embodiments of the disclosure may include at least one of phase difference information, an edge value, and an RGB channel value.

The electronic device according to embodiments of the disclosure may further include a temporary storage device configured to perform control so as to temporarily store the one or more selected images in a memory or a buffer.

In the electronic device according to embodiments of the disclosure, the one or more images to be temporarily stored may be stored in a RAW image format state or in a state in which parameters corresponding to the one or more images to be temporarily stored are applied.

The electronic device according to embodiments of the disclosure may further include a first image-processing device configured to perform at least one of lens shading compensation, black level correction, and defective pixel correction.

The electronic device according to embodiments of the disclosure may further include a second image-processing device configured to perform at least one of demosaicking, denoising, gamma correction, and sharpening.

The electronic device according to embodiments of the disclosure may further include a third image-processing device configured to, if multiple images are selected, compensate for the difference in the field of view between the selected multiple images.

Figure 6:
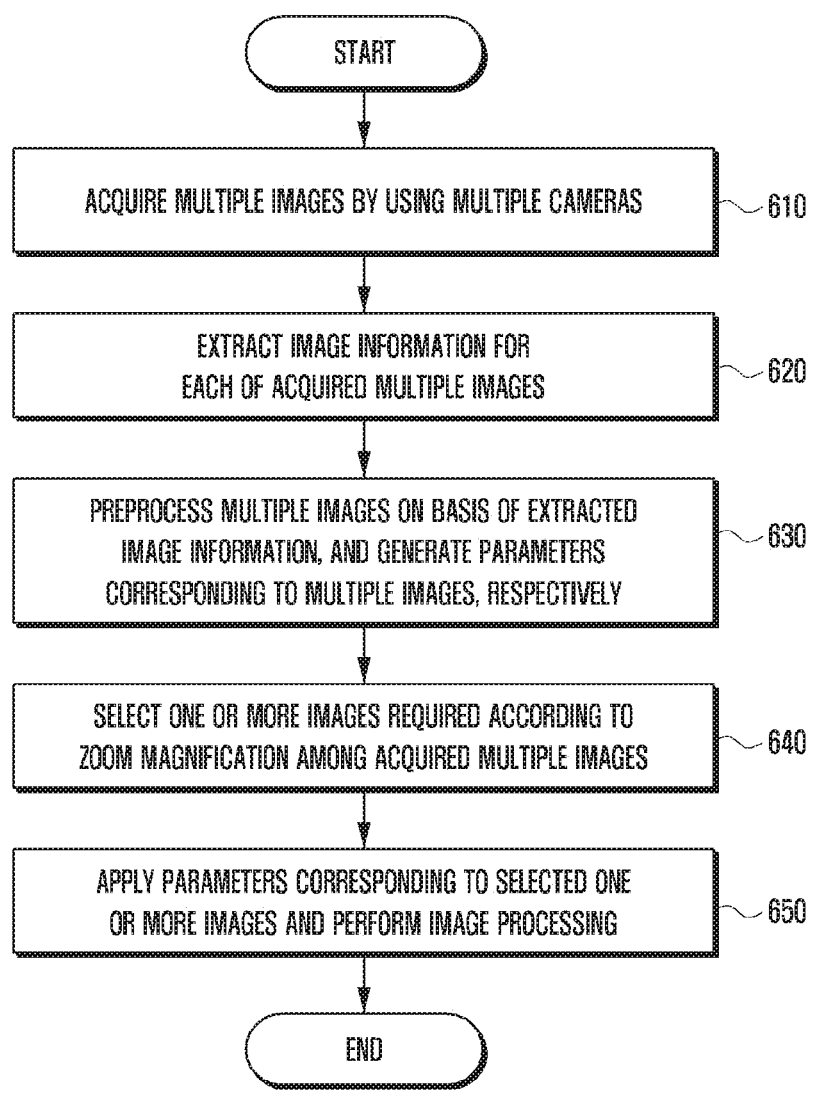
FIG. 6 is a flowchart illustrating a method for processing images according to embodiments of the disclosure.

FIG. 6 is a flowchart illustrating a method for processing images according to embodiments of the disclosure.

Referring to FIG. 6, the electronic device 201 may acquire multiple images using a plurality of cameras 510 (e.g., the camera module 291) in operation 610.

According to embodiments, the plurality of cameras 510 (e.g., the camera module 291) may include cameras having different characteristics (e.g., brightness, focal length, shutter speed, magnification, resolution, field of view, and the like). For example, the first camera 511 and the second camera 512 may include cameras having different focal lengths and/or different fields of view.

According to an embodiment, the plurality of cameras 510 may be a dual camera. The dual camera may include a first camera 511 including a wide angle lens and a second camera 512 including a telephoto lens. For example, the first camera 511 may be configured to focus on the subject, and the second camera 512 may be configured to focus on the background of the subject. Images acquired from the respective cameras described above may be synthesized to produce an optical zoom effect, and may be used for special image-processing such as focusing or defocusing. The images acquired from the plurality of cameras may have a RAW image format, which have not yet processed.

In operation 620, the electronic device 201 may control the image information extracting module 520 so as to extract image information on each of the acquired multiple images.

According to embodiments, the image information extracting module 520 may extract image information from the images photographed by the cameras having different focal lengths and/or different fields of view. The image information may include, for example, phase difference information, an edge value, an RGB channel value, and the like. The phase difference information, the edge value, and the RGB channel value included in the image information may be used to generate parameters for synthesizing the multiple images. In some embodiments, data for performing RGB histogram and auto focus (AF) may be calculated using the extracted image information.

In operation 630, the electronic device 201 may control the image selector 530 so as to preprocess the multiple images on the basis of the extracted image information, thereby generating parameters corresponding to the respective images.

According to embodiments, the electronic device 201 may preprocess the respective images on the basis of the extracted image information. The preprocessing of the images may include, for example, performing operations of auto white balance (AWB), auto exposure (AE), and auto focus (AF). The electronic device 201 may perform the above operations, thereby calculating AF data for focus adjustment, AE data for exposure adjustment, AWB data for white balance adjustment.

According to embodiments, the electronic device 201 may generate parameters for each of the multiple images on the basis of a result of the preprocessing. The parameters may be variables used to perform a variety of image-processing such as zoom adjustment, offset setting, or the like. In addition, the parameters may be used to perform synchronization between the images when the multiple images are synthesized.

In operation 640, the electronic device 201 may control the image selector 530 so as to select one or more images required according to a zoom magnification from among the acquired multiple images.

According to embodiments, the electronic device 201 may predefine the image required according to a zoom magnification. The electronic device 201 may confirm the setting of a zoom magnification, and may select one or more images required according to the confirmation result. For example, the electronic device 201 including a dual camera may acquire a dual image, but in some cases, may require only one of the images depending on the zoom magnification. Processing of unnecessary images may consume power and memory. Therefore, it is possible to select images required according to the zoom magnification before the image-processing.

According to embodiments, if a zoom magnification is changed, and if one or more images suitable for the changed zoom magnification are selected by the function control module, the temporary storage module 532 of the electronic device 201 may perform control such that the one or more selected images are temporarily stored in a memory and/or a buffer. In addition, the images to be temporarily stored in the memory and/or buffer may be stored in the RAW image format, or may be stored in the state in which the parameters corresponding to the one or more selected images are applied.

In operation 650, the electronic device 201 may control the image processor 540 so as to perform image-processing by applying parameters corresponding to the one or more selected images.

According to embodiments, the image processor 540 may process one or more images selected in operation 640. The image-processing may include first image-processing in relation to correction, second image-processing to improve resolution and quality of the image that has been executed with the first image-processing, and third image-processing to compensate for the difference in the field of view between the multiple images. The first image-processing may include, for example, lens shading compensation, black level correction, and defective pixel correction. The second image-processing may include, for example, demosaicking, denoising, gamma correction, and sharpening. When a plurality of images are selected, the third image-processing, for example, may synthesize the plurality of selected images, may improve sharpness and noise, and may compensate for the difference in the field of view between the images.

According to embodiments, the electronic device 201 may control the display so as to display the image that has been executed with the second image-processing or the third image-processing. In addition, the electronic device 201 may store the image that has been executed with the second image-processing or the third image-processing in a memory. A method for processing multiple images according to embodiments of the disclosure may include: acquiring multiple images using a plurality of cameras; extracting image information on each of the acquired multiple images; performing preprocessing for calculating at least one piece of auto focus (AF) data, auto exposure (AE) data, and auto white balance (AWB) data of the multiple images on the basis of the extracted image information and generating parameters corresponding to the respective images; selecting one or more images required according to a zoom magnification from among the acquired multiple images; and performing image-processing by applying parameters corresponding to the one or more selected images.

In the method for processing multiple images according to embodiments of the disclosure, the image information may include at least one of phase difference information, an edge value, and an RGB channel value.

In the method for processing multiple images according to embodiments of the disclosure, the selecting one or more images required according to a zoom magnification from among the acquired multiple images may further include temporarily storing the one or more selected images in a memory or a buffer.

In the method for processing multiple images according to embodiments of the disclosure, the one or more images to be temporarily stored may be stored in a RAW image format state or in a state in which parameters corresponding to the one or more images to be temporarily stored are applied.

In the method for processing multiple images according to embodiments of the disclosure, the image-processing may include first image-processing including at least one of lens shading compensation, black level correction, and defective pixel correction.

In the method for processing multiple images according to embodiments of the disclosure, the image-processing may include second image-processing including at least one of demosaicking, denoising, gamma correction, and sharpening.

In the method for processing multiple images according to embodiments of the disclosure, the image-processing may include third image-processing for, if multiple images are selected, compensating for the difference in the field of view between the selected multiple images.

The method for processing multiple images according to embodiments of the disclosure may further include displaying, on a display, or storing, in a memory, the image acquired by performing the image-processing.

Figure 7:
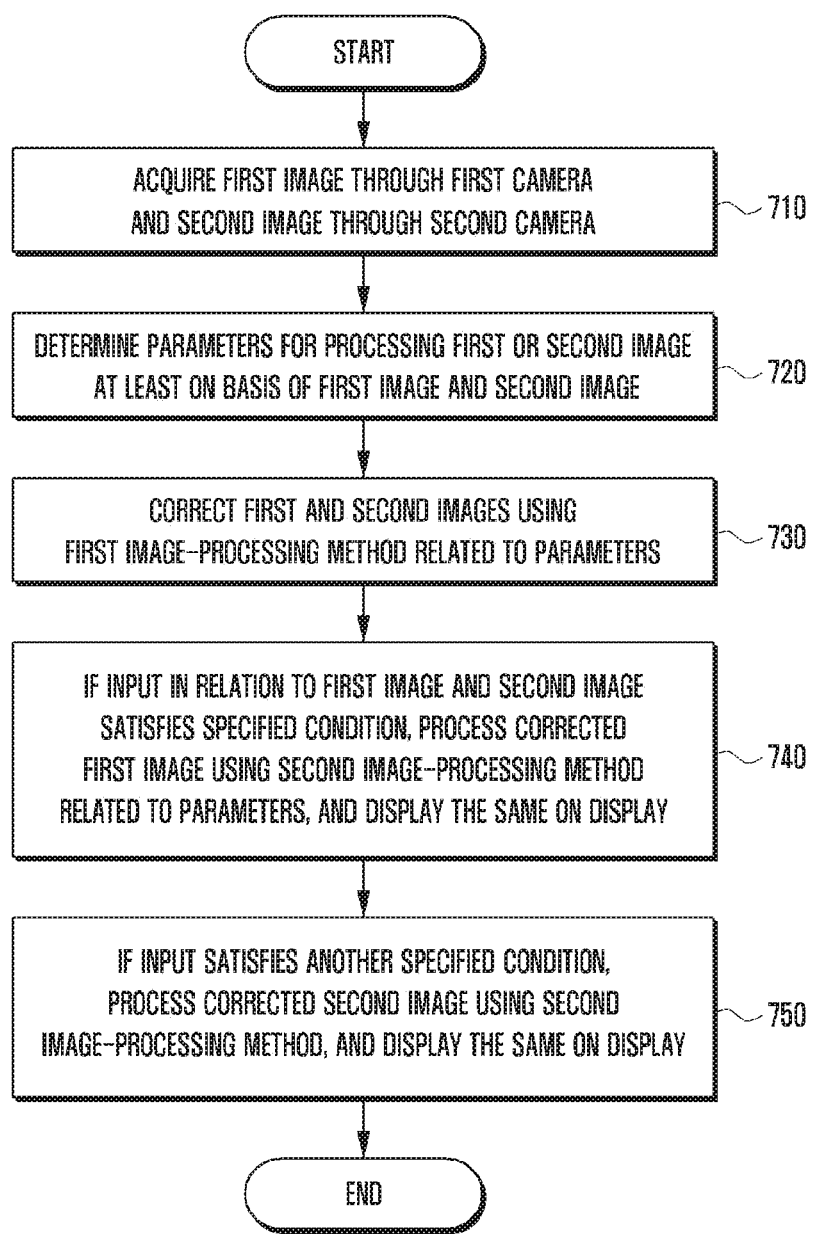
FIG. 7 is a flowchart illustrating a method for displaying images according to embodiments of the disclosure.

FIG. 7 is a flowchart illustrating a method for displaying images according to embodiments of the disclosure.

Referring to FIG. 7, the electronic device 201 may acquire a first image using the first camera and a second image using the second camera in operation 710.

According to embodiments, the first camera 511 and the second camera 512 may include cameras having different focal lengths and/or different fields of view. For example, the first camera may be configured to have a first field of view, and the second camera may be configured to have a second field of view different from the first field of view. For example, the electronic device 201 may include a first camera 511 including a wide angle lens and a second camera 512 including a telephoto lens.

In operation 720, the electronic device 201 may determine parameters for processing the first or second image at least on the basis of a first image and a second image.

According to embodiments, the parameters may include variables for preprocessing or post-processing the acquired images. The parameters may include variables in relation to, for example, preprocessing for calculating at least one piece of auto focus (AF) data, auto exposure (AE) data, and auto white balance (AWB) data of an image, post-processing in relation to correction, post-processing for improving resolution and quality of the corrected image, and post-processing for compensating for the difference in the field of view between the multiple images. In addition, the parameters may be variables used to perform a variety of image-processing such as zoom adjustment, offset setting, or the like. In some embodiments, the parameters may be used to perform synchronization between images when multiple images are synthesized.

In operation 730, the electronic device 201 may correct the first and second images using a first image-processing method related to the parameters.

According to embodiments, the first image-processing method may include adjusting at least one of focus, exposure, or white balance.

In operation 740, if an input in relation to the first image and the second image satisfies a specified condition, the electronic device 201 may process the corrected first image using a second image-processing method related to the parameters, and may display the processed first image on the display.

According to embodiments, if it is determined that an input in relation to the first image and the second image is a user input in relation to a zoom magnification, the electronic device 201, in response to the input, may select at least one image to be displayed on the display from the first and second images.

According to embodiments, the electronic device 201 may set and pre-store images required according to zoom magnifications as a condition. For example, the electronic device 201 may pre-store fields of view, which can be obtained from the first camera. The electronic device 201 may compare an input zoom magnification with a predetermined condition, and if the zoom magnification satisfies the above condition, the electronic device 201 may determine that it corresponds to a field of view that can be displayed using the first image acquired from the first camera, and may perform second image-processing on the first image, thereby displaying the first image, which has been executed with the second image-processing, on the display. The second image-processing may include at least one of, for example, demosaicking, denoising, gamma correction, and sharpening.

In operation 750, if the input satisfies another specified condition, the electronic device 201 may processes the corrected second image using the second image-processing method, and may display the processed second image on the display.

According to embodiments, the electronic device 201 may set and pre-store images required according to zoom magnifications as conditions. For example, the electronic device 201 may pre-store fields of view, which can be obtained from the second camera. The electronic device 201 may compare an input zoom magnification with a predetermined condition, and if the zoom magnification satisfies the predetermined condition, the electronic device 201 may determine that it corresponds to a field of view that can be displayed using the second image acquired from the second camera, and may perform second image-processing on the second image, thereby displaying the second image, which has been executed with the second image-processing, on the display. The second image-processing may include at least one of, for example, demosaicking, denoising, gamma correction, or sharpening.

An electronic device according to embodiments of the disclosure may include: a first camera; a second camera; a processor; and a display operably connected to the processor, wherein the processor is configured to: acquire a first image by means of the first camera and a second image by means of the second camera; determine parameters for processing the first or second image at least on the basis of the first image and the second image; correct the first and second images using a first image-processing method related to the parameters; if an input in relation to the first image and the second image satisfies a specified condition, process the corrected first image using a second image-processing method related to the parameters and display the processed first image on the display; and if the input satisfies another specified condition, process the corrected second image using the second image-processing method and display the processed second image on the display.

The first camera of the electronic device according to embodiments of the disclosure may have a first field of view and the second camera may have a second field of view different from the first field of view.

The first image-processing method of the electronic device according to embodiments of the disclosure may include adjusting at least one of focus, exposure, or white balance.

The processor of the electronic device according to embodiments of the disclosure may be configured to select at least one image to be displayed on the display from among the first and second images in response to a user input, as the input, in relation to a zoom magnification.

The second image-processing method of the electronic device according to embodiments of the disclosure may be configured to include at least one of demosaicking, denoising, gamma correction, or sharpening.

An electronic device according to embodiments of the disclosure may include: a first camera configured to acquire a first image; a second camera configured to acquire a second image; and a processor, wherein the processor is configured to: acquire image information using the first and second images; perform first image-processing in relation to the first and second images on the basis of the image information; select at least one image to be displayed on the display from the first and second images; perform second image-processing in relation to the at least one image on the basis of the image information; and display the at least one image on a display operably connected to the processor.

The "module" used in this document may include a unit including hardware, software or firmware and may be interchangeably used with a term, for example, logic, a logical block, a part or a circuit. The "module" may be an integrated part, a minimum unit to perform one or more functions, or a part thereof. The "module" may be implemented mechanically or electronically, and may include an application-specific integrated circuit (ASIC) chip, field-programmable gate arrays (FPGAs) or a programmable logic device which performs some operations and which has been known or is to be developed, for example. At least some of a device (e.g., modules or functions thereof) or method (e.g., operations) according to various embodiments may be implemented as instructions stored in a computer-readable storage medium (e.g., the memory 130) in the form of a program module. If the instructions are executed by a processor (e.g., the processor 120), the processor may perform functions corresponding to the instructions. The computer-readable storage medium may include a hard disk, a floppy disk, magnetic media (e.g., magnetic tape), optical media (e.g., CD-ROM), a DVD, magneto-optical media (e.g., a floptical disk), and embedded memory. The instructions may include code generated by a compiler or code executable by an interpreter. The module or program module according to various embodiments may include at least one of the aforementioned elements, may omit some of the elements or may further include other elements. Operations performed by the module, program module or other elements according to various embodiments may be executed in a sequential, parallel, repetitive or heuristic manner or at least some operations may be executed in a different sequence or omitted or may further include other operations.

The invention claimed is:

1. An electronic device comprising:
   a processor; and
   a plurality of cameras configured to acquire multiple images;
   wherein the processor is configured to:
      extract image information on each of the acquired multiple images;
      perform preprocessing for calculating at least one piece of auto focus (AF) data and auto exposure (AE) data of the multiple images on the basis of the extracted image information;
      generate parameters corresponding to the respective images based on the extracted image information including phase difference information, an edge value, and an RGB channel value;
      select one or more images required according to a zoom magnification from among the acquired multiple images; and
      perform and synthesize image-processing of the one or more selected images from the acquired multiple images, based on parameters of the one or more selected images,
   wherein the parameters include variables related to zoom adjustment, offset setting, and synchronization between the acquired multiple images.

2. The electronic device of claim 1, further comprising a temporary storage device configured to perform control so as to temporarily store the one or more selected images in a memory or a buffer, wherein the one or more images to be temporarily stored are stored in a RAW image format state or in a state in which parameters corresponding to the one or more images to be temporarily stored are applied.

3. The electronic device of claim 1, wherein the processor is further configured to perform at least one of lens shading compensation and defective pixel correction.

4. The electronic device of claim 3, wherein the processor is further configured to:
- perform at least one of demosaicking, denoising and sharpening; or
- if multiple images are selected, compensate for the difference in the field of view between the selected multiple images.

5. A method for processing multiple images, the method comprising:
- acquiring multiple images using a plurality of cameras;
- extracting image information on each of the acquired multiple images;
- performing preprocessing for calculating at least one piece of auto focus (AF) data and auto exposure (AE) data of the multiple images on the basis of the extracted image information and generating parameters corresponding to the respective images based on the extracted image information including phase difference information, an edge value, and an RGB channel value;
- selecting one or more images required according to a zoom magnification from among the acquired multiple images; and
- performing and synthesizing image-processing of the one or more selected images from the acquired multiple images, based on parameters of the one or more selected images,
- wherein the parameters include variables related to zoom adjustment, offset setting, and synchronization between the acquired multiple images.

6. The method of claim 5, wherein the selecting one or more images required according to a zoom magnification from among the acquired multiple images further comprises temporarily storing the one or more selected images in a memory or a buffer, and
- wherein the one or more images to be temporarily stored are stored in a RAW image format state or in a state in which parameters corresponding to the one or more images to be temporarily stored are applied.

7. The method of claim 5, wherein the image-processing comprises:
- first image-processing including at least one of lens shading compensation and defective pixel correction;
- second image-processing including at least one of demosaicking, denoising and sharpening; or
- third image-processing for, if multiple images are selected, compensating for the difference in the field of view between the selected multiple images.

8. The method of claim 5, further comprising displaying, on a display, or storing, in a memory, the image acquired by performing the image-processing.

* * * * *